(12) United States Patent
Fischer et al.

(10) Patent No.: US 6,551,803 B1
(45) Date of Patent: Apr. 22, 2003

(54) METHOD FOR PURIFICATION OF AMINO ACID CONTAINING SOLUTIONS BY ELECTRODIALYSIS

(75) Inventors: Andreas Fischer, Ludwigshafen (DE); Christoph Martin, Mannheim (DE); Jürgen Müller, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/111,919

(22) PCT Filed: Nov. 3, 2000

(86) PCT No.: PCT/EP00/10852

§ 371 (c)(1),
(2), (4) Date: May 1, 2002

(87) PCT Pub. No.: WO01/32298

PCT Pub. Date: May 10, 2001

(30) Foreign Application Priority Data

Nov. 3, 1999 (DE) .......................... 199 52 961

(51) Int. Cl.⁷ .......................... C12P 13/04; C12P 13/08; B01D 61/44
(52) U.S. Cl. .................. 435/106; 435/107; 435/108; 435/109; 435/110; 435/113; 435/114; 435/115; 435/116; 435/262; 204/527; 204/530; 204/534; 204/537
(58) Field of Search ................. 435/106, 107, 435/108, 109, 110, 113, 114, 115, 116, 262; 204/534, 527, 530, 537

(56) References Cited

U.S. PATENT DOCUMENTS

| | | | | |
|---|---|---|---|---|
| 4,882,277 A | * | 11/1989 | Czytko et al. | 435/136 |
| 4,909,916 A | * | 3/1990 | Koberstein et al. | 204/534 |
| 5,002,881 A | | 3/1991 | Van Nispen et al. | |
| 5,049,250 A | * | 9/1991 | Chilanda | 204/534 |
| 5,567,293 A | * | 10/1996 | Paleologou et al. | 204/523 |
| 5,645,703 A | * | 7/1997 | Tsai | 204/538 |
| 6,110,342 A | * | 8/2000 | Mani | 204/527 |

FOREIGN PATENT DOCUMENTS

| | | |
|---|---|---|
| EP | 0 381 134 | 1/1990 |
| JP | 52 001092 | 1/1977 |
| JP | 52 066686 | 6/1977 |
| JP | 55 064767 | 5/1980 |
| JP | 59 22608 | 2/1984 |
| JP | 01 102049 | 4/1989 |
| WO | 91/02548 | 3/1991 |

OTHER PUBLICATIONS

WPI Abstract 1977–12130Y JP52001092 Published Jan. 1977.*
WPI Abstract 1984–066204 JP59022608 Published Feb. 1984.*
WPI Abstract 1980–45634C JP55064767 Published May 1980.*
WPI Abstract 1977–49652Y JP52066686Y JP19750142029 Published Jun. 1977.*
J. Sandeaux et al.: "Extraction of amino acids from protein hydrolysates by electrodialysis" J. Chem. Tchnol. Biotechnol., vol. 71, pp. 267–273.

* cited by examiner

*Primary Examiner*—Herbert J. Lilling
(74) *Attorney, Agent, or Firm*—Oblon, Spivak, McClelland, Maier & Neustadt, P.C.

(57) ABSTRACT

A process is described for purifying an amino acid-containing solution by means of electrodialysis, wherein an amino acid-containing solution is employed which is obtained from the fermentation for producing at least one amino acid.

9 Claims, 3 Drawing Sheets

METHOD FOR PURIFICATION OF AMINO ACID CONTAINING SOLUTIONS BY ELECTRODIALYSIS

Figure 1:
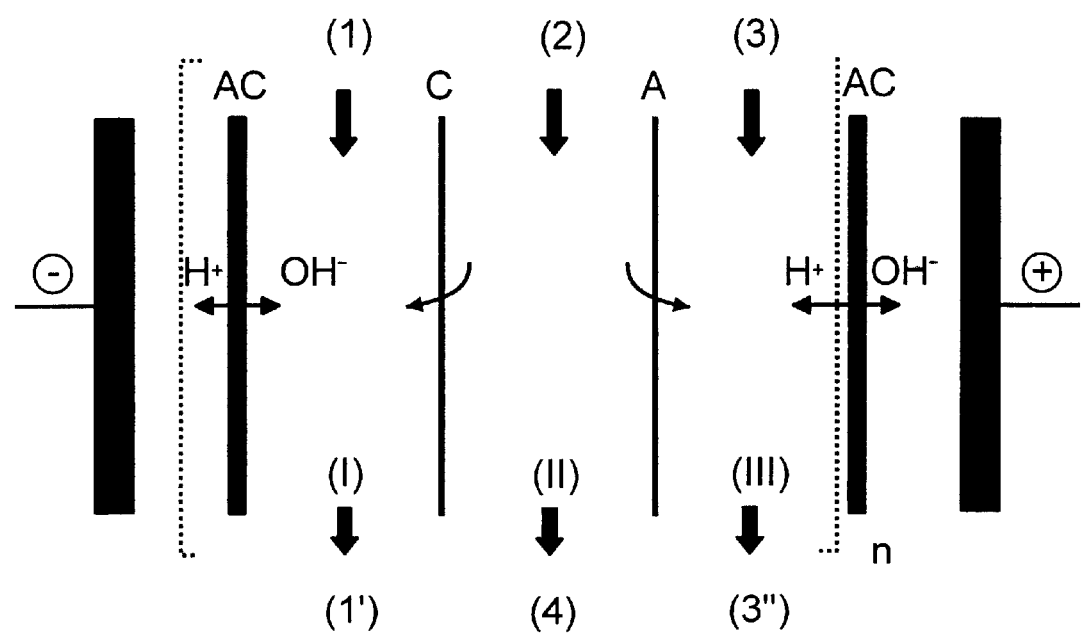

The present invention relates to a process for purifying amino acid-containing solutions by electrodialysis, an amino acid-containing solution being employed which is obtained from a fermentation.

Amino acids can be produced from a carbon source such as, for example, molasses and raw sugar by means of fermentation. The solutions generally accumulating in the fermentation contain in addition to about 10% by weight of amino acid large amounts of contaminants such as, for example, also biomass.

According to the processes used up until now in accordance with the prior art numerous process steps are necessary for purifying this solution obtained from a fermentation in order to produce the amino acid in the commonly marketed form, for example as lysine hydrochloride. Usually, large amounts of salts such as, for example, ammonium sulfate accumulate, approximately 1 kg of ammonium sulfate per kg of amino acid being generated as a product of value. Additionally, large amounts of wastewater accumulate and have to be worked up and disposed of. A preferably commercially used process for working up discharges from amino acid fermentation is essentially based on ion exchange treatment. The discharges from the fermentation are mixed with acid and then loaded onto a cation exchange column or an anion exchange column. The amino acid in its ionic form displaces the corresponding ions of the cation or anion exchange column and thus is retained by the column. The biomass can be filtered off before or after the ion exchange treatment. The mother liquor obtained after passage still contains approximately 0.1% by weight of amino acid and a load of about 1 metric ton of salt, for example ammonium sulfate, per metric ton of amino acid. This solution can be disposed of by dumping at sea which is objectionable, in particular ecologically, owing to the high salt load of the solution to be dumped at sea.

As an alternative to this, the mother liquor which contains essentially ammonium sulfate and biomass may be worked up in numerous evaporation and filtration stages, it being possible for ammonium sulfate to be retrieved. However, the accumulating mother liquor has still to be disposed of. Moreover, this procedure is very labor-intensive and has a high energy consumption.

The amino acid retained on the ion exchange resin is eluted, for example, with aqueous ammonia. Ammonia is stripped off the accumulating eluate, large amounts of aqueous ammonia having to be evaporated. The eluted amino acid is then mixed with acid, for example hydrochloric acid, crystallized and dried. The amino acid obtained in this way is >98.5% pure and is called "feed-grade" amino acid. In order to obtain even less contaminated, so-called "food-grade" or "pharma-grade" amino acid, feed-grade product has to be subjected to a further purification procedure, for example active carbon treatment and/or repeated crystallization. Further details with respect to the purification processes in accordance with the prior art described above can be found in the PERP report 5357. The specifications food-grade and pharma-grade used here refer to the relevant purity requirements according to the US FDA, where the appropriate standard for lysine HCl is to be understood correspondingly or analogously. According to this, the term "with high purity" used here also refers to the food-grade or pharma-grade standard for lysine according to the US FDA and is in this context also used either correspondingly or analogously.

Electrodialysis is a very elegant purification or separation process which can fractionate, inter alia, mixtures of amino acids. A process of this type is described, for example, by Sandeaux et al. in J. Chem. Technol. Biotechnol. 71 (1998), pp. 267 ff. According to this scientific publication, protein hydrolysates obtained by acidic hydrolysis of animal residues or human residues such as, for example, feathers or hairs are initially neutralized and decolorized by activated carbon and then subjected to a multistage electrodialysis, various fractions of the individual amino acids being obtained.

WO 91/02584 describes a process for removing amphoteric compounds from aqueous solutions by means of 3-cycle electrodialysis with bipolar membranes.

U.S. Pat. No. 5,002,881 describes a fermentation process for producing lactic acid by a combination of microfiltration, reverse osmosis and electrodialysis. U.S. Pat. No. 4,882,277 discloses a further process for removing organic acids from fermentation broths by means of anion exchange membranes and producing the free acid by bipolar membranes.

The above summary of the prior art reveals that the purification of amino acids from discharges from fermentations has up until now merely been carried out by means of ecologically disadvantageous and/or costly processes.

It was an object of the present invention to provide an improved process for purifying amino acid from discharges from fermentations. This object was achieved by applying electrodialysis to this problem.

Accordingly, the present invention relates to a process for purifying amino acid-containing solutions by electrodialysis (d), an amino acid-containing solution being employed which is obtained from a fermentation for producing at least one amino acid.

Using this process it is possible to avoid numerous process steps which are indispensable according to the processes of the prior art. Large amounts of ammonium sulfate or other extraneous salts are not generated inevitably in this case. Electrodialysis carried out in a suitable way makes it further possible to produce amino acid as free base or free acid. It is further possible to obtain high amino acid yields of preferably >90%, further preferably >95%, based on the employed amount of amino acid at high current densities and therefore correspondingly high capacities of the electrodialysis. Accordingly, the present invention also relates to the use of electrodialysis for purifying amino acid-containing solutions obtained from the fermentation up to an amino acid content of >98.5% (% by weight).

As stated above, the process according to the invention relates to the purification of amino acid-containing solutions which are obtained from the fermentation. It is possible to employ here generally all amino acid-containing solutions obtainable by the various fermentation processes. Further stages such as, for example, ion exchange treatment and/or crystallization may be carried out between the actual fermentation process and the electrodialysis, merely the resulting mother liquor then being treated by means of electrodialysis.

Therefore the present invention also relates to a process comprising the following additional stages (a) to (c):

(a) treatment by means of an ion exchanger of an amino acid-containing solution obtained from the fermentation for producing at least one amino acid, (b) crystallization of an amino acid-containing solution obtained in (a), where an amino acid-containing mother liquor is obtained, and (c) introduction of the amino acid-containing mother liquor obtained in (b) into an electrodialysis apparatus.

Besides the mentioned process stages, further stages such as, for example, filtration before stage (a) may be carried out.

Figure 2:
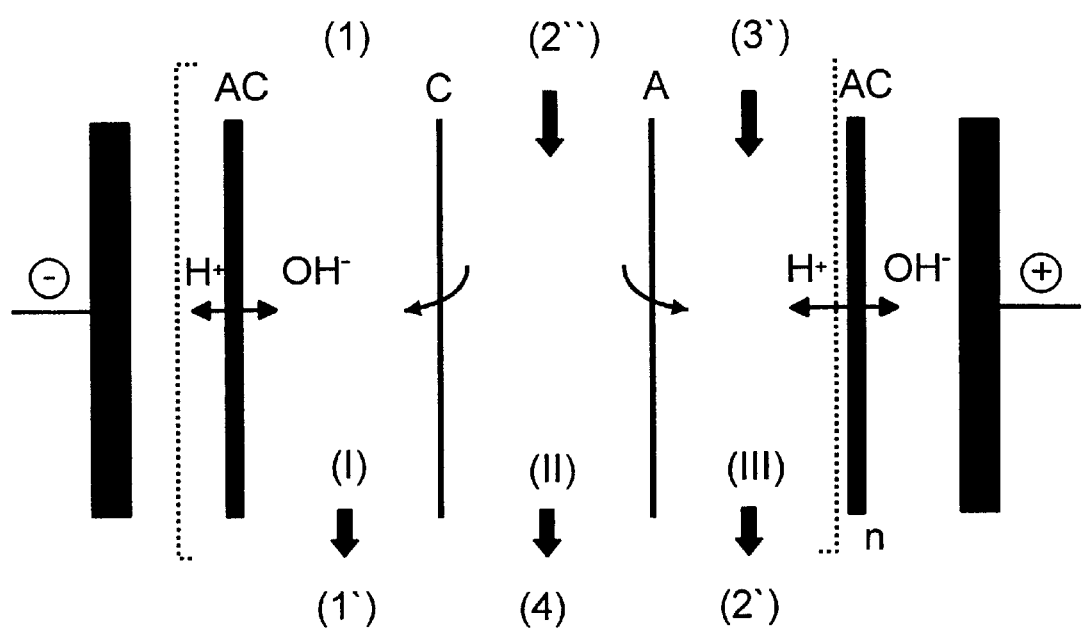
Figure 3:
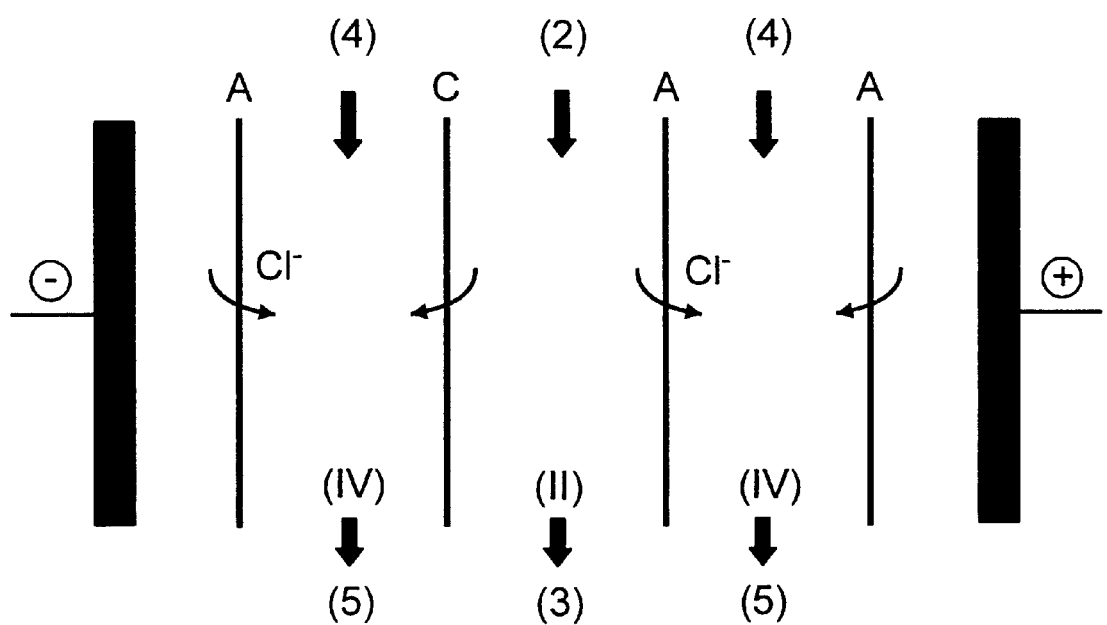

FIG. 1 describes an embodiment of the present invention, which employs a 3-cycle electrodialysis with bipolar membranes;

FIG. 2 also describes a further embodiment of the present invention, which uses a 3-cycle electrodialysis;

FIG. 3 describes an embodiment of the present invention, which uses a conventional 2-cycle electrodialysis.

In principle, all amino acids can be employed as amino acids within the scope of the process according to the invention. This includes, for example, amino acids having positively charged (basic) side groups such as, for example, lysine, arginine, histidine; amino acids having negatively charged (acidic) side groups such as, for example, aspartic acid or glutamic acid; and amino acids having uncharged, polar or nonpolar side groups such as, for example, alanine, valine, leucine, isoleucine, proline, phenylalanine, tryptophan, methionine, glycine, serine, threonine, cysteine, tyrosine, asparagine and glutamine.

Within the scope of the present invention either 3-cycle electrodialysis with bipolar membranes is applied for purifying the amino acid-containing solutions, it thus being possible to produce amino acid as free base or free acid, or conventional dual-cycle electrodialysis is applied in which the amino acid accumulates as a salt, preferably as an amino acid hydrochloride, for example, as lysine hydrochloride.

The following section gives a short overview of these two electrodialysis methods.

Conventional dual-cycle electrodialysis used for the purpose of the present invention is known per se and is described in EP-B-0 381 134, whose contents relating to conventional dual-cycle electrodialysis are included in their entirety in the present application.

A sketch of the principle of this electrodialysis arrangement is shown in FIG. 3.

The apparatus employed in this variant of electrodialysis has a positive (anode (+)) and a negative (cathode (−)) large-area electrode. The space between these electrodes is divided up by a large number of alternately arranged cation (C) and anion (A) exchange membranes in a large number of narrow chambers which are separated from one another by the membranes and which are also referred to as diluate cycle (II) and concentrate cycle (IV). In this arrangement, chambers which have an anion exchange membrane on the cathode side and a cation exchange membrane on the anode side are called concentrate chambers or concentrate cycles, while chambers which have the anion exchange membrane on the anode side and the cation exchange membrane on the cathode side form the diluate chambers or the diluate cycle.

To carry out the process according to the invention, the diluate cycles are filled with the amino acid-containing solution to be purified (2), the concentrate cycles, however, are filled with an aqueous electrolyte (4) and the chambers in which the electrodes are located and, where appropriate, also the chambers directly adjacent thereto are charged with an electrode rinsing solution, usually a sodium sulfate solution.

Under the influence of the voltage applied to the electrodes, the ions migrate through the membrane which is permeable to them from the diluate cycle into the concentrate cycle. Further migration through the following membrane which is impermeable to the relevant type of ions is impossible, and the ion thus remains in the concentrate cycle. The liquids in the diluate, concentrate and electrode cycles are separately circulated by pump, where appropriate with interpolated reservoirs. In this arrangement the desired amino acid (5) accumulates in the concentrate cycle as a salt of high purity such as, for example, highly pure lysine hydrochloride. A lysine-free mother liquor (3) accumulates in the diluate cycle which is charged with the solution to be purified (2), for example with a solution of lysine hydrochloride.

In principle, any membranes commonly used for the purpose of electrodialysis processes may be employed for carrying out the process according to the invention. Commercial ion exchange membranes are preferably employed in the electrodialysis carried out for the purpose of the present process. These membranes preferably consist of organic polymers having ionic side chains. Cation exchange membranes contain sulfonate or carboxyl groups in the polymer matrix, while anion exchange membranes have tertiary or quaternary amino groups as substituents of the polymeric base material. Copolymers of styrene and divinylbenzene are particularly suitable as polymeric base material for the ion exchange membranes. Ion exchange membranes having a capacity of from 0.8 to 5, preferably 1.2 to 3.2 milliequivalents per g (meq/g), are preferably employed. Examples of anion exchange membranes which can be used are: Tokuyama AM1, AM2, AM3, AMX, AMH, AFN, Asahi Glass AMV. Examples of cationic exchange membranes which may be mentioned are Tokuyama CM1, CM2, CMX, CMH and Asahi Glass CMV.

As a modification of the conventional 2-cycle electrodialysis disclosed in EP-B 0 381 134, it is also possible to employ a membrane arrangement using bipolar membranes. Bipolar membranes are laminates of anion and cation exchange membranes. They are distinguished from monopolar anion and cation exchange membranes by efficiently catalyzing water cleavage in the electric field for the electrodialysis, and thus also serve to provide $H^+$ and $OH^-$ equivalents.

A 3-cycle (chamber) arrangement (3-cycle bipolar electrodialysis) consisting of diluate(II), acid(III) and base (I) cycles is used. The 3-cycle arrangement is achieved by an alternating sequence of the particular ion exchange membranes (cf. FIG. 1):

....CA I C II A III....

C=cation exchange membrane; CA=bipolar membrane;
M=anion exchange membrane;
I=base cycle; II diluate cycle; III =acid cycle;

The electrodialysis is preferably carried out at about 10 to about 80° C., in particular from about 20 to about 60° C. The current density of conventional 2-cycle electrodialysis varies from about 1 to about 1000 $A/m^2$, preferably from about 100 to about 800 $A/m^2$. In 3-cycle bipolar electrodialysis the current density varies from about 1 to about 1500 $A/m^2$, preferably from about 200 to about 1000 $A/m^2$.

Within the process according to the invention, electrodialysis is carried out until the final conductivity of the diluate is about 2 mS/cm, in particular about 1 mS/cm and below, for example about 0.8 or 0.5 mS/cm. In principle, all amino acids can be removed in this manner, if the isoelectric point is passed in the direction of lower pH by adding acid and thus the amino acid receives an excess positive charge or if the isoelectric point of the amino acid is passed in the direction of higher pH by adding base and the amino acid in this way receives a negative overall charge. In the first case, the amino acid enters the base cycle through the cation exchange membrane in the direction of the cathode where it accumulates as free base. In the latter case, the amino acid migrates in anionic form into the acid cycle through the anion exchange membrane in the direction of the anode where it accumulates as free acid.

When using conventional electrodialysis, the corresponding salt of the amino acid is always obtained in the concentrate chamber.

In the following, the purification by means of electrodialysis is illustrated in greater detail by the example of lysine, an amino acid with a positively charged (basic) side group, with reference to the appended figures. However, the procedure described can be applied analogously to all of the remaining abovementioned amino acids.

When using a 3-cycle electrodialysis with bipolar membranes, a solution containing lysine in cationic from (H-lysine$^+$), for example as lysine*HCl, is introduced into the diluate chamber of the electrodialysis and subsequently transferred into the so-called base cycle through a cation exchange membrane. From protonated lysine now present in the base cycle, lysine base is liberated by hydroxide ions formed at the bipolar membrane. The anions, for example chloride or sulfate ions, are transferred through an anion exchange membrane into the so-called acid cycle chamber and form the corresponding acid together with the protons released there at the bipolar membrane. The diluate chamber retains uncharged particles such as, for example biomass, so that purification of lysine occurs simultaneously. In order to avoid unwanted reactions of solution components, the electrodes are rinsed with an electrolyte solution in a separate circulation.

FIG. 1 explains the principle of this process. It is to be noted that the arrangement depicted merely represents one unit of the electrodialysis apparatus used. Such units may be employed according to the invention in electrodialysis apparatuses having 1 to 1000 units. AC indicates a bipolar membrane, C a cation exchange membrane and A an anion exchange membrane. The dotted line indicates that the unit shown may be present more than once in the electrodialysis apparatus, "n" giving the number of repetitions. The acid corresponding to the accumulating lysine-containing solution, for example hydrochloric acid or sulfuric acid (3), is introduced as acid cycle charge into the acid cycle (III). The maximum dilution is chosen, it merely being necessary to ensure that the ionic conductivity of the solution at the start of the electrodialysis is sufficient. Generally, concentrations of 0.5% by weight are employed. A dilute solution of free lysine (1) which may originate, for example, from an already purified batch is employed as charge in the base cycle (I). The solutions introduced into both the acid cycle and the base cycle may be purified within the electrodialysis. Thus it is possible, for example, to fill the acid cycle (III) with 0.5% strength $H_2SO_4$ it being possible for the $H_2SO_4$, concentration to increase up to about 10% during electrodialysis. In the base cycle (I) the solution employed which contains lysine as free base in a concentration of, for example, 0.5%, is generally concentrated up to a concentration of lysine as free base of from 10 to 30% (1'). The acid formed in the acid cycle chamber may in turn serve to prepare the lysine salt of the acid from lysine monohydrate liberated during electrodialysis or to acidify the discharge from the fermentation for use in electrodialysis. Such an acidified discharge from the fermentation, for example lysine*$H_2SO_4$, (2), is introduced using said 3-cycle electrodialysis via the diluate cycle (II), a lysine-free mother liquor of the fermentation (4) being obtained in the diluate cycle (II). As already indicated above, cationic lysine migrates during electrodialysis through a cation exchange membrane into the base cycle (I), while the counterions reach the acid cycle (III) via an anion exchange membrane. The bipolar membrane also present provides the acid cycle with $H^+$ ions and the base cycle with $OH^-$ ions.

In order to obtain, for example, solid lysine monohydrate from lysine accumulating as free base in the base cycle, the discharge from the base cycle merely has to be evaporated, the method of spray drying being preferred here. In order to obtain the corresponding salts such as, for example, amino acid hydrochloride or sulfate, the amino acid hydrate-containing solution has to be mixed with the corresponding acids or bases. Lysine obtained in this way has a purity of >98.5%, corresponding to the feed-grade specification, and may be purified further, for example, by simple activated carbon treatment or re-crystallization, so that food-grade or pharma-grade lysine is also obtainable. As an alternative to this, it is also possible to forgo nearly complete removal of lysine from the diluate cycle or carry out fractionating electrodialysis and thus obtain food-grade or pharma-grade lysine without further measures. In this case, the amino acid is removed from the diluate up to a certain degree of depletion and transferred with a high current yield; contaminants are substantially retained.

A further embodiment of the present invention is shown in FIG. 2. In this case, the lysine-containing solution from the fermentation is introduced into the acid cycle (III) in non-acidified form (3') in which lysine is present in monohydrate form. Lysine is obtained thereby in a cationic form, for example as lysine*$H_2SO_4$ (2'), and thus an acidified discharge from the fermentation is obtained. This can then be introduced in the next batch as diluate (2") into the diluate cycle (II) and be purified as described above; the other reference symbols in FIG. 2 correspond to those in FIG. 1. This variant has the advantage that only in the first batch does the diluate charge, i.e. the discharge from the fermentation, have to be acidified once, and it is possible in the further course of the electrodialysis to forgo further addition of acid.

Accordingly, the present invention also relates to a process as defined above which comprises:

(d1) introducing the amino acid-containing solution obtained from the fermentation into the acid cycle or base cycle of a 3-cycle electrodialysis with bipolar membranes (A), the amino acid being obtained in cationic form in the acid cycle or in basic form in the base cycle; and (d2) introducing the amino acid obtained in (d1) in cationic or anionic form into the diluate cycle of a further 3-cycle electrodialysis with bipolar membranes (B) with production of amino acid as free base in the base cycle or acid cycle.

As explained, using the 3-cycle electrodialysis with a bipolar membrane initially produces free lysine base which may either be obtained directly from solid lysine monohydrate by drying and can be sold or is initially mixed with hydrochloric acid and subsequently dried, lysine hydrochloride in this case being obtained.

If lysine in cationic form, for example lysine hydrochloride, is to be obtained as product of value, it is also possible to employ so-called conventional electrodialysis without bipolar membranes. This procedure is depicted diagrammatically in FIG. 3. Conventional electrodialysis comprises an alternating arrangement of cation exchange membranes (C) and anion exchange membranes (A). In an arrangement of this type the lysine-containing solution (2) containing lysine as a salt, for example lysine hydrochloride, can be introduced into the so-called diluate chamber (II). During electrodialysis lysine in cationic form reaches the concentrate cycle (IV) via the cation exchange membrane (C). The corresponding counterions, for example chloride ions, migrate from the diluate cycle (II) into the concentrate cycle via the anion exchange membrane (A). In the process, purified lysine salt (5), for example lysine hydrochloride, is obtained in the concentrate chamber, while uncharged contaminants (3) remain in the diluate chamber.

Accordingly, the present invention relates to an integrated process for producing a free amino acid, which comprises:
- (I) production of an amino acid-containing solution by fermentation starting from a suitable carbon source, preferably molasses, raw sugar or a mixture of both, and
- (II) treatment of the amino acid-containing solution obtained in (I) by means of a process as defined above.

The process according to the invention using electrodialysis for purifying lysine-containing solutions provides in comparison with processes of the prior art particular advantages:
1. Expenditure on equipment is distinctly less;
2. No extraneous salts accumulate which have to be expensively disposed of;
3. Amino acids can be produced directly as their free bases or acids.
4. Comparatively small amounts of wastewater accumulate.
5. No ammonia and, according to FIG. 2, no acid either has to be employed for working up the discharges of the fermentation.

In the following the present invention is to be illustrated by means of examples.

EXAMPLES

Example 1
(Removal of Lysine from Contaminated Solution by Means of 3-cycle Electrodialysis with Bipolar Membranes to Produce Free Lysine Base)

In an electrodialysis cell comprising an alternating arrangement of cation exchange membranes (Tokuyama CMX), anion exchange membranes (Tokuyama AM3) and bipolar membranes (Aqualytics polysulfone) according to FIG. 1 and having 10 chambers, 2 kg of a 40% by weight lysine hydrochloride solution (feed-grade quality) were employed as diluate cycle charge.

Electrodialysis was carried out at a maximum current density of 80 mA/cm$^2$ at an applied cell voltage of 35 V and 50° C. After a current input of 25 Ah a discharge from the base cycle containing 32% by weight of lysine base with a residual chloride content of under 0.2% by weight was obtained with a lysine yield of 96% of the initial charge. The iodine color number of a lysine hydrochloride solution adjusted to 10% by weight corresponding to the diluate charge was 14, that of a correspondingly adjusted, lysine-base containing discharge from the base cycle was 1.85. Consequently, distinct purification occurred with simultaneous liberation of the lysine base.

Example 2
(Removal of Lysine Hydrochloride from Contaminated Solutions by Means of Conventional Electrodialysis)

In an electrodialysis cell comprising an alternating arrangement of cation exchange membranes (Tokuyama CMX) and anion exchange membranes (Tokuyama AM3) according to FIG. 3 and having 5 chambers, 1 kg of a 40% by weight lysine hydrochloride solution (feed-grade quality) was employed as diluate cycle charge. 0.5 kg of a 0.5% by weight lysine hydrochloride solution was employed as concentrate cycle charge.

Electrodialysis was carried out at a maximum current density of 80 mA/cm$^2$ at an applied cell voltage of 20 V and 50° C. After 8 hours of electrodialysis, a discharge from the base cycle containing 29% by weight of lysine hydrochloride was obtained with a yield of >98% of the initial charge. The iodine color number of a lysine hydrochloride solution adjusted to 10% by weight from the discharge from the concentrate cycle of the electrodialysis was 1.1. Distinct purification of the lysine hydrochloride also occurred.

List of reference symbols

| | |
|---|---|
| I Base cycle | AC Bipolar membrane |
| II Diluate Cycle | C Cation exchange membrane |
| III Acid cycle | A Anion exchange membrane |
| IV Concentrate cycle | n further units |

FIG. 1:

| | |
|---|---|
| (1) | Lysine free base (0.5%) |
| (1') | Lysine free base (10–30%) |
| (2) | Lysine × H$_2$SO$_4$ (acidified discharge from the fermenter) |
| (4) | Lysine-free discharge from the fermenter |
| (3) | H$_2$SO$_4$ (0.5%) |
| (3") | H$_2$SO$_4$ (5–10%) |

FIG. 2:

| | |
|---|---|
| (1) | Lysine free base |
| (1') | Lysine free base (higher concentration) |
| (2') | Lysine × H$_2$SO$_4$ (acidified discharge from the fermenter) |
| (2") | Lysine × H$_2$SO$_4$ (ex acid cycle from previous batch) |
| (3') | Lysine (discharge from the fermenter) |
| (4) | Lysine-free discharge from the fermenter |

FIG. 3:

| | |
|---|---|
| (4) | Lysine in cationic form (reaches IV via C) |
| (5) | Lysine × HCl (pure) |
| (2) | Lysine * HCl (contaminated) |
| (3) | Lysine-free mother liquor |

What is claimed is:

1. A process for purifying an amino acid-containing solution by means of electrodialysis (d), characterized in that an amino acid-containing solution is employed which is obtained from a fermentation for producing at least one amino acid, wherein said amino acid-containing solution is purified by mean of a 3-cycle electrodialysis with bipolar membranes and the amino acid is obtained as free amino acid.

2. The process as claimed in claim 1, characterized in that the amino acid-containing solution has at least one amino acid selected from: lysine, arginine, histidine, aspartic acid, glutamic acid, alanine, valine, leucine, isoleucine, proline, phenylalanine, tryptophan, methionine, glycine, serine, threonine, cysteine, tyrosine, asparagine and glutamine.

3. The process as claimed in claim 2, characterized in that the amino acid-containing solution contains lysine in cationic form as the amino acid.

4. The process as claimed in claim 1, wherein said purification is employed by means of a 3-cycle electrodialysis and comprises following stages:

(d1) introducing the amino acid-containing solution obtained from the fermentation into the acid cycle or base cycle of a 3-cycle electrodialysis with bipolar membranes (A), the amino acid being obtained in cationic form in the acid cycle or in basic form in the base cycle; and (d2) introducing the amino acid obtained in (d1) in cationic or anionic form into the diluate cycle of a further 3-cycle electrodialysis with bipolar membranes (B) with production of amino acid as free base in the base cycle or acid cycle.

5. The process as claimed in claim 1, which additionally comprises the following further steps which are carried out between fermentation and the purification by means of electrodialysis:
   (a) treatment by means of an ion exchanger of an amino acid-containing solution obtained from fermentation for producing at least one amino acid,
   (b) crystallization of an amino acid-containing solution obtained in (a), where an amino acid-containing mother liquor is obtained, and
   (c) introduction of the amino acid-containing mother liquor obtained in (b) into an electrodialysis apparatus.

6. The process as claimed in claim 1, wherein the amino acid is obtained in a purity of >98.5% (% by weight).

7. An integrated process producing a free amino acid, which comprises:
   (I) production of an amino acid-containing solution by fermentation starting from a carbon source, and
   (II) purifying the amino acid-containing solution obtained in (I) using the process of claim 1.

8. The process as claimed in claim 7, wherein the carbon source is selected from the group consisting of molasses, raw sugar, and mixtures of both.

9. The process as claimed in claim 1, wherein said amino acid is obtained as the free amino acid in the discharge of the 3-cycle electrodialysis.

* * * * *